United States Patent [19]

Nishizawa et al.

[11] Patent Number: 5,502,264
[45] Date of Patent: Mar. 26, 1996

[54] METHOD OF PREPARING UNSATURATED DIMERS OF α-METHYLSTYRENES

[75] Inventors: Hiroshi Nishizawa; Takayuki Saitoh; Tatsuo Itoh; Kiyotaka Mashita, all of Ichihara, Japan

[73] Assignee: Goi Chemical Company, Ltd., Chiba, Japan

[21] Appl. No.: 245,670

[22] Filed: May 18, 1994

[30] Foreign Application Priority Data

Sep. 6, 1993 [JP] Japan .................................. 5-243536

[51] Int. Cl.6 ................................................ C07C 2/04
[52] U.S. Cl. ...................... 585/406; 585/435; 585/510; 585/515; 585/526
[58] Field of Search .................................... 585/406, 510, 585/513, 515, 526, 435

[56] References Cited

U.S. PATENT DOCUMENTS 2,249,987  7/1941  Stanley et al. .
4,596,896  6/1986  Cobb ........................................ 585/320

FOREIGN PATENT DOCUMENTS 2439762  5/1980  France .
416335   4/1965  Japan .

OTHER PUBLICATIONS

Database WPI, Section CH, Week 9142, Derwent Publications Ltd.

*Primary Examiner*—Ponnathapura Achutamurthy
*Attorney, Agent, or Firm*—Antonelli, Terry, Stout & Kraus

[57] ABSTRACT

1-pentene dimers of α-methylstyrenes are produced with high selectivity in good productivity by stirring 50 to 95 parts by weight of an α-methylstyrene in the presence of 50 to 5 parts by weight of an aqueous solution of a sulfonic acid, and a 1-pentene dimer having good preservative property is then collected by removing the sulfonic acid, adjusting the resulting reaction solution to pH 8 or higher and distilling the neutralized reaction solution.

18 Claims, No Drawings

METHOD OF PREPARING UNSATURATED DIMERS OF α-METHYLSTYRENES

BACKGROUND OF THE INVENTION

1. Field of the Invention

The present invention relates to a method of preparing unsaturated dimers of α-methylstyrenes which are suitably used as agents for controlling molecular weight in the production of copolymers, such as SBR.

2. Description of Related Art

In production of copolymers, such as acrylonitrile butodiene-styrene (ABS) resins, acrylonitrile styrene (AS) resins, polystyrene and styrene butadiene rubber (SBR), tetrachloromethane or dodecylmercaptans have been used as agents for controlling molecular weight. However, as to tetrachloromethane, which destroys the ozone layer, its abolition by the end of 1995 was settled at the Montreal International Conference in 1992, and the use of dodecylmercaptans has come to be restricted due to regulations concerning odor pollution caused during handling and uses. These agents therefore have come to be substituted by unsaturated dimers of α-methylstyrenes, particularly by 1-pentene dimers, but there is not yet reported any industrial method for producing 1-pentene dimers in good selectivity.

In Japanese Patent Application Kokoku Koho (publication) No. 41-6335 is disclosed a conventional method of preparation of unsaturated dimers of α-methylstyrenes wherein α-methylstyrenes are dimerized by using sulfonic acids as catalysts. The method however is poor in the selectivity toward 1-pentene dimers since the catalysts are in direct contact with the α-methylstyrenes. Further, since the resulting unsaturated dimers of α-methylstyrenes decompose readily on distillation with heat under acidic conditions caused by the presence of the catalysts, the method needs complicated steps preceding to the distillation, for example, removal of the catalysts from reaction solutions by filtration, by neutralization with a large amount of an alkali or by rinsing with water or an aqueous alkali solution. Even the unsaturated dimers resulting from such complicated steps and distillation involve a problem. That is, the unsaturated dimers purified by the distillation are free of problems for a while, but are so poor in preservative property as to get colored during storage.

SUMMARY OF THE INVENTION

An object of the present invention is to provide a method of preparing unsaturated dimers of α-methylstyrenes whereby α-methylstyrenes are dimerized in high selectivity and good productivity into 1-pentene dimers which are among unsaturated dimers of α-methylstyrenes.

The result of the inventors' study for achieving the object has proved that among various unsaturated dimers of α-methylstyrenes, 1-pentene dimers can be produced in good selectivity and high productivity by using as catalysts sulfonic acids in a state of aqueous solution and by using α-methylstyrenes and the aqueous solution of sulfonic acids in weight ratios of 50:50 to 95:5. Based on the knowledge, the inventors have completed the present invention.

That is, the present invention provides a method of preparing an unsaturated dimer of an α-methylstyrene comprising dimerizing the α-methylstyrene by stirring 50 to 95 parts by weight of the α-methylstyrene in the presence of 50 to 5 parts by weight of an aqueous solution of a sulfonic acid.

Taking dimers of α-methylstyrene by way of example to describe dimers of α-methylstyrenes, the dimers include one saturated dimer, namely 1,1,3-trimethyl-3-phenylindane (SD1), and two unsaturated dimers, namely 2,4-diphenyl-4-methyl-1-pentene (UD1) and 2,4-diphenyl-4-methyl-2-pentene (UD2). According to the present invention, α-methylstyrene (AMS) is scarcely dimerized into the saturated dimer but is dimerized highly selectively to 2,4-diphenyl-4-methyl-1-pentene, which is one of the unsaturated dimers and has excellent preservative property. Even before purification by distillation, 1-pentene dimers are obtainable, for example, in an yield of 90% or more.

Some examples of the α-methylstyrene to be used in the present invention include α-methylstyrene, m-methyl-α-methylstyrene, p-methyl-α-methylstyrene, m-ethyl-α-methylstyrene, p-ethyl-α-methylstyrene, m-isopropyl-α-methylstyrene and p-isopropyl-α-methylstyrene. Particularly preferred is α-methylstyrene.

Some examples of the aqueous solution of the sulfonic acid include aqueous solutions of o-toluenesulfonic acid, m-toluenesulfonic acid, p-toluenesulfonic acid, o-phenolsulfonic acid, m-phenolsulfonic acid, p-phenolsulfonic acid, methanesulfonic acid, ethanesulfonic acid, benzenesulfonic acid, naphthalene-α-sulfonic acid, naphthalene-β-sulfonic acid or a mixture thereof. Particularly preferred is an aqueous solution of p-toluenesulfonic acid.

In the method of the present invention, 50 to 5 parts by weight of the aqueous solution of the sulfonic acid is used per 50 to 95 parts by weight of the α-methylstyrene. That is, the weight ratio of the α-methylstyrene:the aqueous solution of the sulfonic acid is 50:50 to 95:5. Within the range of the weight ratio of 50:50 to 95:5, the reaction system is in a state where the aqueous solution of the sulfonic acid is dispersed in a continuous phase of the α-methylstyrene, thereby increasing the selectivity toward unsaturated dimers of the α-methylstyrene. An amount of the α-methylstyrene less than the above-described range makes a reaction system wherein the α-methylstyrene is dispersed in a continuous phase of the aqueous solution of the sulfonic acid, thereby decreasing the selectivity toward the unsaturated dimers of the α-methylstyrene, and an amount of the aqueous solution of the sulfonic acid less than the above-described range lengthens the reaction time. The preferred range of the weight ratio of the α-methylstyrene:the aqueous solution of the sulfonic acid is 60:40 to 85:15.

The concentration of the sulfonic acid in the aqueous solution of the sulfonic acid is preferably 30 to 80% by weight, more preferably 45 to 80% by weight, particularly preferably 60 to 75% by weight. A concentration of less than 30% by weight lengthens the reaction time, and if the concentration is more than 80% by weight, the sulfonic acid becomes difficult to dissolve in water and may precipitate in the reaction system.

The reaction temperature is preferably 20° to 90° C., more preferably 30° to 80° C., particularly preferably 40° to 70° C. If the reaction temperature is lower than 20° C., the progress of the reaction may be slow, and a reaction temperature of higher than 90° C. may decrease the selectivity. The preferred range of the reaction time is 0.5 to 24 hours, more preferably 4 to 16 hours. The reaction proceeds efficiently under ambient pressure or under elevated pressure.

It is preferable to agitate vigorously the α-methylstyrene and the aqueous solution of the sulfonic acid. When the weight ratio of the α-methylstyrene to the aqueous solution of the sulfonic acid is in the claimed range, vigorous agitation makes the reaction proceed in a system where the aqueous solution of the sulfonic acid is dispersed in a continuous phase of the α-methylstyrene, and the selectivity toward the 1-pentene dimer is increased.

Thus the 1-pentene dimer of the α-methylstyrene is produced in high productivity. Purification of the 1-pentene dimer is carried out preferably by removing the sulfonic acid to obtain a reaction solution, adjusting the reaction solution to pH 8 or higher by adding an alkali, and then distilling the dimer of the α-methylstyrene from the reaction solution.

For example, the removal of the sulfonic acid may be performed easily by cooling the reaction mixture resulting from the above-described reaction to room temperature, allowing the cooled reaction mixture to stand to separate and collecting the upper layer of a reaction solution (oily layer). After an alkali is added to the upper layer of the reaction solution (oily layer) obtained to adjust pH to 8 or higher, preferably 9 to 11, purification by distillation is carried out to obtain purified, unsaturated dimers of the α-methylstyrene, which have excellent preservative property. If the distillation is carried out at a pH of lower than 8, the resulting unsaturated dimers of the α-methylstyrene will be poor in preservative property. The separation and collection of the unsaturated dimers of the α-methylstyrene formed by the reaction and the aqueous solution of the sulfonic acid used as the catalyst can be performed easily since the two separate from each other readily after the reaction with agitation. Also the method of the present invention is economically advantageous since the aqueous solution of the sulfonic acid may be used repeatedly.

When sulfonic acids are used as catalysts, neutralizing reaction mixtures to pH 7 by rinsing with water or neutralization prevents decomposition or isomerization of unsaturated dimers of α-methylstyrenes during distillation. However, distillation at a pH of lower than 8 deteriorates the preservative property of the purified products. This seems to be caused by traces of free sulfonic acids which remain the reaction mixture even after the virtual neutralization of the reaction mixture. It appears that traces of free sulfonic acids, which do not cause decomposition or isomerization of the unsaturated dimers of α-methylstyrenes during distillation, cause some bad effect on the preservative property as storage is lengthened. The amounts of the free sulfonic acids in reaction mixtures seem to be so decreased as to have no influence on preservative property only when the reaction mixtures are adjusted to pH 8 or higher. However, it is not yet clear whether the direct cause for the deterioration of preservative property is the free sulfonic acids remaining in purified products. That is, it is not clear whether the free sulfonic acids still remain as such in the purified products obtained by distillation, and also it it not clear whether the deterioration of preservative property is caused by the free sulfonic acid themselves.

The method of the distillation in the purification stage is not particularly limited, and a preferred method is vacuum distillation. The conditions for the distillation are not particularly limited, and the distillation is carried out preferably under vacuum of 5 to 50 mmHg at 120° to 230° C.

The preferred examples of the alkali are salts which are reaction products of a weak acid and a strong base, such as $K_2CO_3$, $Na_2CO_3$, $K_3PO_4$ and $Na_3PO_4$. These alkalis may be used individually or in a combination of two or more. Particularly preferred is $K_2CO_3$.

The present invention will be described in more detail with reference to the following Examples. These Examples, however, are not to be construed to limit the scope of the invention.

EXAMPLES 1 TO 6 AND COMPARATIVE EXAMPLES 1 TO 3

Example 1

To 90.0 g of α-methylstyrene (AMS) was added 10.0 g of a 60% by weight aqueous solution of p-toluenesulfonic acid (PTS) monohydrate which was prepared by dissolving 12.0 g of p-toluenesulfonic acid monohydrate in 8.0 g of water, and the mixture was heated to 70° C. under vigorous agitation of about 300 rpm with agitating blades. The weight ratio of the aqueous solution of PTS monohydrate/AMS was 10/90, and the reaction system was observed to consist of a continuous phase of AMS and a dispersion phase of the aqueous PTS solution dispersed in the continuous phase. Agitation was continued at 70° C. for 20 hours until the conversion percentage of α-methylstyrene reached 90%.

The reaction mixture obtained was cooled to room temperature and was then allowed to stand to collect a reaction solution (oily layer) which was separated as the upper layer. 100 g of the reaction solution (oily layer) was adjusted to pH 11 by addition of 0.28 g of 25% aqueous solution of $K_2CO_3$, and was then directly subjected to vacuum distillation, to obtain purified, unsaturated dimers of α-methylstyrene. The selectivity toward unsaturated dimers was 100%, with a high selectivity toward 2,4-diphenyl- 4-methyl-1-pentene of 91%. The results are listed in Table 1.

EXAMPLES 2 AND 3 AND COMPARATIVE EXAMPLE 1

The same procedure as that of Example 1 was repeated with the exception that the weight ratio of the aqueous solution of PTS monohydrate/AMS and the reaction time were varied as listed in Table 1. The results are listed in Table 1.

In each of the reaction systems within the claimed weight ratio of aqueous PTS solution/AMS, the aqueous solution of p-toluenesulfonic acid was dispersed in a continuous phase of α-methylstyrene, and a high selectivity toward 2,4-diphenyl-4-methyl-1-pentene was attained. On the other hand, in Comparative Example 1 wherein the weight ratio was beyond the claimed range, α-methylstyrene was dispersed in a continuous phase of the aqueous solution of p-toluenesulfonic acid, so that the selectivity toward 2,4-diphenyl-4-methyl-1-pentene was lower than those of Examples.

TABLE 1

|  | Examples | | | Comp. Ex. |
| --- | --- | --- | --- | --- |
|  | 1 | 2 | 3 | 1 |
| Aqueous solution of PTS monohydrate/AMS (weight ratio) | 10/90 | 20/80 | 35/65 | 60/40 |
| Concentration of PTS monohydrate in aqueous solution (wt %) | 60 | 60 | 60 | 60 |
| Reaction conditions | | | | |
| Reaction temperature (°C.) | 70 | 70 | 70 | 70 |
| Reaction time (h)*[1] | 20 | 16 | 8 | 4 |
| Selectivity toward unsaturated dimers at 90% conversion of AMS (%) | 100 | 100 | 100 | 99.1 |
| Selectivity toward | 91 | 92 | 91 | 86 |

TABLE 1-continued

| | Examples | | | Comp. Ex. |
|---|---|---|---|---|
| | 1 | 2 | 3 | 1 |
| UD1 at 90% conversion of AMS (%)*[2] | | | | |
| Reaction system | | | | |
| (dispersed phase /continuous phase) | Aq. PTS /AMS | Aq. PTS /AMS | Aq. PTS /AMS | AMS /Aq. PTS |

*[1]The time when the conversion of AMS reached 90%.

*[2]Selectivity = $\frac{UD1}{UD1 + UD2} \times 100$

EXAMPLE 4

To 80.0 g of α-methylstyrene (AMS) was added 20.0 g of a 60% by weight aqueous solution of p-toluenesulfonic acid (PTS) monohydrate which was prepared by dissolving 12.0 g of p-toluenesulfonic acid monohydrate in 8.0 g of water, and the mixture was heated to 70° C. under vigorous agitation with agitating blades at about 300 rpm. The weight ratio of the aqueous solution of PTS monohydrate/AMS was 20/80, and the reaction system was observed to consist of a continuous phase of AMS and a dispersion phase of the aqueous PTS solution dispersed in the continuous phase. Agitation was continued at 70° C. for 14 hours until the conversion percentage of α-methylstyrene reached 90%.

The reaction mixture obtained was cooled to room temperature and was then allowed to stand to collect a reaction solution (oily layer) which was separated as the upper layer. 100 g of the reaction solution (oily layer) was adjusted to pH 11 by addition of 0.28 g of 25% aqueous solution of K₂CO₃, and was then directly subjected to vacuum distillation (vacuum: 7 mmHg, temperature: 120°–220 ° C.), to obtain purified, unsaturated dimers of α-methylstyrene. The purified product did not contain AMS monomer or saturated dimers but showed a selectivity toward unsaturated dimers of 100%, including a high selectivity toward 2,4-diphenyl-4-methyl-1-pentene of 97%. The results of evaluation of preservative property of the purified product are listed in Table 2.

EXAMPLES 5 AND 6 AND COMPARATIVE EXAMPLES 2 AND 3

The same procedure as that of Example 4 was repeated with the exception that the alkali added and the pH during distillation were varied as listed in Table 1. The results of evaluation of preservative property of the purified products are listed in Table 2. Distilling reaction solutions after adjustment of pH within the claimed range provided unsaturated dimers having excellent preservative property.

TABLE 2

| | Reaction solution | Alkali added | pH during distillation | Preservative property (60° C.) Hue | | | |
|---|---|---|---|---|---|---|---|
| | | | | 0 | 30 | 45 | 60 |
| | | | | | (days) | | |
| Ex. 4 | 100 g | 25% Aq. K₂CO₃ 0.28 g | 11 | 10 | 10 | 10 | 10 |
| Ex. 5 | 100 g | 25% Aq. K₂CO₃ 0.20 g | 9 | 10 | 10 | 10 | 10 |
| Ex. 6 | 100 g | 5% Aq. KOH 0.82 g | 12 | 10 | 10 | 10 | 50 |
| Comp. Ex. 2 | 100 g | 25% Aq. K₂CO₃ 0.12 g | 7 | 10 | 10 | 80 | 100 |
| Comp. Ex. 3 | 100 g | 5% Aq. KOH 0.30 g | 7 | 10 | 10 | 80 | 100 |

The evaluation of preservative property was conducted by allowing samples to stand at 60° C. and measuring hue of the samples according to ASTM D-1209.

What is claimed is:

1. A method of preparing an unsaturated dimer of an α-methylstyrene comprising dimerizing the α-methylstyrene by stirring 50 to 95 parts by weight of the α-methylstyrene at a temperature of 20° to 90° C. for 0.5 to 24 hours in the presence of 50 to 5 parts by weight of an aqueous solution of a sulfonic acid; the aqueous solution of the sulfonic acid having a concentration of sulfonic acid of 30 to 80% by weight.

2. The method of claim 1, wherein the α-methylstyrene is selected from the group consisting of unsubstituted α-methylstyrene, m-methyl-α-methylstyrene, p-methyl-α-methylstyrene, m-ethyl-α-methylstyrene, p-ethyl-α-methylstyrene, m-isopropyl-α-methylstyrene, p-isopropyl-α-methylstyrene and a mixture thereof.

3. The method of claim 2, wherein the α-methylstyrene is unsubstituted α-methylstyrene.

4. The method of claim 1, wherein the sulfonic acid is selected from the group consisting of o-toluenesulfonic acid, m-toluenesulfonic acid, p-toluenesulfonic acid, o-phenolsulfonic acid, m-phenolsulfonic acid, p-phenolsulfonic acid, methanesulfonic acid, ethanesulfonic acid, benzenesulfonic acid, naphthalene-α-sulfonic acid, naphthalene-β-sulfonic acid and a mixture thereof.

5. The method of claim 4, wherein the sulfonic acid is p-toluenesulfonic acid.

6. The method of claim 5, wherein the α-methylstyrene is unsubstituted α-methylstyrene.

7. The method of claim 1, wherein the dimerization is carried out at a temperature of 20° to 90° C.

8. The method of claim 7, wherein the aqueous solution of the sulfonic acid has a concentration of the sulfonic acid of 30 to 80% by weight, the α-methylstyrene is selected from the group consisting of α-methylstyrene, m-methyl-α-methylstyrene, p-methyl-α-methylstyrene, m-ethyl-α -methylstyrene, p-ethyl-α-methylstyrene, m-isopropyl-α -methylstyrene, p-isopropyl-α-methylstyrene and a mixture thereof and the sulfonic acid is selected from the group consisting of o-toluenesulfonic acid, m-toluenesulfonic acid, p-toluenesulfonic acid, o-phenolsulfonic acid, m-phenolsulfonic acid, p-phenolsulfonic acid, methanesulfonic acid, ethanesulfonic acid, benzenesulfonic acid, naphthalene-α-sulfonic acid, naphthalene-β-sulfonic acid and a mixture thereof.

9. The method of claim 8, wherein the α-methylstyrene is unsubstituted α-methylstyrene and the sulfonic acid is p-toluenesulfonic acid.

10. The method of claim 1, wherein after the α-methylstyrene is dimerized and the sulfonic acid is removed to obtain a reaction solution, the reaction solution is adjusted to pH 8 or higher by adding an alkali metal base, and the dimer of the α-methylstyrene is then distilled from the reaction solution.

11. The method of claim 10, wherein the reaction solution is adjusted to pH 9 to 11.

12. The method of claim 10, wherein the α-methylstyrene is unsubstituted α-methylstyrene.

13. The method of claim 10, wherein the alkali metal base is an alkali metal salt of a weak acid and an alkali metal hydroxide.

14. The method of claim 13, wherein the alkali metal base is selected from the group consisting of $K_2CO_3$, $Na_2CO_3$, $K_3PO_4$, $Na_3PO_4$ and a mixture thereof.

15. The method of claim 14, wherein the alkali metal base is $K_2CO_3$.

16. The method of claim 13, wherein the α-methylstyrene is selected from the group consisting of unsubstituted α-methylstyrene, m-methyl-α-methylstyrene, p-methyl-α-methylstyrene, m-ethyl-α-methylstyrene, p-ethyl-α-methylstyrene, m-isopropyl-α-methylstyrene, p-isopropyl-α-methylstyrene and a mixture thereof, the sulfonic acid is selected from the group consisting of o-toluenesulfonic acid, m-toluenesulfonic acid, p-toluenesulfonic acid, o-phenolsulfonic acid, m-phenolsulfonic acid, p-phenolsulfonic acid, methanesulfonic acid, ethanesulfonic acid, benzenesulfonic acid, naphthalene-α-sulfonic acid, naphthalene-β-sulfonic acid and a mixture thereof, and the reaction solution is adjusted to pH 9 to 11.

17. The method of claim 16, wherein the α-methylstyrene is unsubstituted α-methylstyrene, the sulfonic acid is p-toluenesulfonic acid, and the alkali metal base is $K_2CO_3$.

18. The method of claim 1, further comprising recovering dimers of the α-methylstyrene from the aqueous solution of the sulfonic acid, said dimers comprising a 1-pentene dimer.

* * * * *